(12) United States Patent
Hwang et al.

(10) Patent No.: US 8,053,386 B2
(45) Date of Patent: Nov. 8, 2011

(54) HETEROPOLY ACID CATALYST AND METHOD OF PREPARING THE SAME

(75) Inventors: Gyo-hyun Hwang, Daejeon (KR); Min-ho Kil, Daejeon (KR); Hyun-kuk Noh, Daejeon (KR); Won-ho Lee, Daejeon (KR); Min-suk Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 97 days.

(21) Appl. No.: 12/312,824

(22) PCT Filed: Nov. 29, 2007

(86) PCT No.: PCT/KR2007/006081
§ 371 (c)(1),
(2), (4) Date: Oct. 15, 2009

(87) PCT Pub. No.: WO2008/066329
PCT Pub. Date: Jun. 5, 2008

(65) Prior Publication Data
US 2010/0069230 A1    Mar. 18, 2010

(30) Foreign Application Priority Data
Dec. 1, 2006    (KR) .................... 10-2006-0120604

(51) Int. Cl.
| | | |
|---|---|---|
| B01J 27/198 | (2006.01) | |
| B01J 27/00 | (2006.01) | |
| B01J 27/188 | (2006.01) | |
| B01J 27/19 | (2006.01) | |
| B01J 27/192 | (2006.01) | |
| B01J 23/00 | (2006.01) | |
| B01J 23/32 | (2006.01) | |

(52) U.S. Cl. ........ 502/209; 502/208; 502/210; 502/211; 502/212; 502/303; 502/304; 502/305; 502/311; 502/312; 502/317; 502/318; 502/319; 502/320; 502/321; 502/322; 502/323; 502/324; 502/337

(58) Field of Classification Search .......... 502/208–212, 502/301–355
See application file for complete search history.

(56) References Cited

U.S. PATENT DOCUMENTS

| | | | | |
|---|---|---|---|---|
| 2,180,353 | A * | 11/1939 | Foster ............................ | 502/353 |
| 4,003,978 | A * | 1/1977 | Shiraishi et al. .............. | 423/237 |
| 4,307,247 | A * | 12/1981 | Shaw et al. .................... | 562/599 |
| 4,564,607 | A * | 1/1986 | Yoneda et al. ................. | 502/209 |
| 4,596,784 | A | 6/1986 | Kennelly et al. | |
| 5,173,468 | A * | 12/1992 | Boehning et al. ............. | 502/209 |
| 5,221,767 | A * | 6/1993 | Boehning et al. ............. | 562/532 |
| 5,422,326 | A | 6/1995 | Kuroda et al. | |
| 5,681,790 | A | 10/1997 | Kim et al. | |

* cited by examiner

*Primary Examiner* — Patricia L Hailey
(74) *Attorney, Agent, or Firm* — McKenna Long & Aldridge LLP

(57) ABSTRACT

The present invention relates to a heteropoly acid catalyst which is used for the production of methacrylic acid by gas phase oxidation of methacrolein and a preparing method thereof. The present invention, thereby, provides a novel heteropoly acid catalyst having excellent methacrolein conversion rate, methacrylic acid selectivity and yield.

6 Claims, No Drawings

HETEROPOLY ACID CATALYST AND METHOD OF PREPARING THE SAME

This application claims the benefit of International Application No. PCT/KR2007/006081 filed Nov. 29, 2007 along with Korean Application No. 10-2006-0120604, filed on Dec. 1, 2006, both of which are hereby incorporated by reference for all purposes as if fully set forth herein.

TECHNICAL FIELD

The present invention relates to a heteropoly acid catalyst and a preparing method of the same, more precisely a novel heteropoly acid catalyst used for the production of methacrylic acid by gas phase oxidation of methacrolein and a preparing method of the same with excellent methacrolein conversion, methacrylic acid selectivity and yield.

BACKGROUND ART

The total demand for methyl methacrylate (MMA) in the world wide market is now over 2 million tons and Asia, USA and Europe lead the market. In Asia, the demand for MMA in 2000 was approximately 750,000 tons, which was 4-5% increased from the previous year (400,000 tons in Japan; 110,000 tons in Taiwan; 90,000 tons in Korea; 80,000 tons in China and 70,000 tons in others). MMA demand in Asia is expected to increase further by an average of 4-5% per year owing to the growing demand in each country including China, Japan and others.

In Asia, MMA monomer has been mostly used for copolymer resins such as acrylonitrile-styrene (AS) and acrylonitrile-butadiene-styrene (ABS), paints for buildings and cars, paper coating, plastic, and resin modifier such as methylmethacrylate-butadiene-styrene (MBS).

In spite of the increasing demand for MMA, the production of acrylonitrile byproduct has been always short and thereby new production methods have been tried. One example is the gas phase oxidation based production established by Nippon Shokubai in 1982, which was the first in the world that uses isobutylene as a raw material. Since then, Mitsubishi Rayon, Sumitomo Chemical, and Kuraray/Mitsui Chemicals have initiated industrialization of MMA monomer by taking advantage of the gas phase oxidation. Another example is MAN process developed by Asahi Kasei by using methacrylonitrile (MAN). Mitsubishi Gas Chemical succeeded in industrialization of MMA by using novel acetone cyanohydrin (ACH) method which does not generate waste acid. KMC and FPC in Taiwan produce MMA by ACH method, while LG MMA and Honam Petrochemical Corp. in Korea, That MMA in Thailand and Singapore MMA Monomer in Singapore produce MMA by gas phase oxidation method.

Studies on the catalyst containing heteropoly acid as an active ingredient which is used for the partial oxidation of methacrolein into methacrylic acid by gas phase oxidation have been continued since the first commercialization in 1980s.

To produce heteropoly acid, $MoO_3$ and $V_2O_5$ precursors are reacted with $H_3PO_4$ in the presence of water solvent at the temperature of at least 80° C. or ammonium paramolybdate and ammonium paravanadate are dissolved together in water. Details of the methods are described in the publication made by Tsigdinos, et al (Inorganic Chemistry, 7(3), p 437 (1968)).

U.S. Pat. No. 4,558,028 (granted on Dec. 10, 1985) describes a catalyst represented by $Mo_aP_bA_cB_dC_eD_fO_x$ (A is one or more elements selected from the group consisting of As, Sb, Ge, Bi, Zr and Se; B is one or more elements selected from the group consisting of Cu, Fe, Cr, Ni, Mn, Co, Sn, Ag, Zn and Rh; C is one or more elements selected from the group consisting of V, W, and Nb; D is one or more elements selected from the group consisting of alkali metals, alkali earth metals and Ti; a is 12; b is 0.5-4; c is 0-5; d is 0-3; e is 0-4; f is 0.01-4 and x is the value indicating the oxidation of each element). The catalyst that is defined as the above needs to be dried, molded and fired in the presence of oxygen or nitrogen at 300-500° C. to be a final catalyst product. In general, the catalyst is molded as a pellet of 5 mm in diameter and 5 mm in length and at this time, decomposable ammonium or nitrate salt is decomposed to be a catalyst having the right structure and composition.

U.S. Pat. No. 4,621,155 (granted on Nov. 4, 1986) describes a method of preparing a heteropoly acid catalyst in which nitrogen containing pyridine, piperidine or peperazine is additionally included to increase plasticity, physical strength and reproducibility of catalyst production.

This method of preparing a heteropoly acid catalyst depends on the precursor of a metal component, but generally nitrate $(NO_3^-)$ is used.

U.S. Pat. No. 6,333,293B1 (granted on Dec. 25, 2001) describes a method of preparing a catalyst. In this method, ammonium paramolybdate and ammonium paravanadate are dissolved in heated water, followed by stirring. Then, proper amount of 85% $H_3PO_4$ is added thereto and cesium nitrate and copper nitrate are additionally added. The mixed solution is heated and dried to give a catalyst.

U.S. Pat. No. 6,458,741B2 (granted on Oct. 1, 2002) describes a method of preparing a catalyst. In this method, ammonium paramolybdate, ammonium metavanadate and pyridine are added to 85% $H_3PO_4$, to which nitric acid, cesium nitrate and copper nitrate are additionally added, followed by co-precipitation. Then the precipitate is heated and dried to give a catalyst. According to this patent, the ratios of $NH_4/Mo_{12}$ and $NH_4/NO_3$ included in the precursor affect the activity and selectivity of the catalyst.

In spite of the development of various methods for producing a heteropoly acid catalyst, the low activity of the conventional heteropoly acid catalyst is still a problem. Therefore, it is required to improve the methacrolein conversion rate and selectivity in gas phase oxidation and the low productivity resulted from low yield as well.

DISCLOSURE OF INVENTION

Technical Problem

It is an object of the present invention, to overcome the problems of the conventional methods, to provide a novel heteropoly acid catalyst having improved methacrolein conversion rate, methacrylic acid selectivity and yield and a preparing method of the same.

Technical Solution

The above object and other objects of the present invention can be achieved by the following embodiments of the present invention.

To achieve the above object, the present invention provides a novel heteropoly acid catalyst represented by the following formula 1.

$$PMo_{12}V_aCs_bK_cX_dY_e(Q(PO_4)_f)_gO_x \qquad \text{ChemistryFigure 1}$$

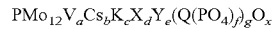

Wherein, X is one or more metal components selected from the group consisting of Cu, Ag, Co, Pb, Mn and Ti; Y is one or more metal components selected from the group consisting of As, Sb, Bi, Zn and Nb; Q is one or more metal components selected from the group consisting of Cr, La, Ce, Fe, Ni and Mg; a is $0.1<a<3$; b is $0.5<b<3$; c is $0<c<1$; d is $0<d<3$; e is $0<e<3$; f is $0.5<f<3$; g is $0.001<g<3$; x is the number satisfied with atomic values of a, b, c, d, e, f and g.

The present invention also provides a method of preparing a heteropoly acid catalyst comprising the following steps:

(a) preparing an aqueous solution by mixing $MoO_3$, $V_2O_5$ and $H_3PO_4$ with a distilled water;

(b) preparing a slurry by adding dropwise an aqueous solution prepared by mixing Cs and K precursors, a metal precursor and pyridine to the prepared aqueous solution; and (c) drying and firing the slurry.

The present invention is described in detail hereinafter.

The present inventors have studied on a heteropoly acid catalyst and completed this invention by confirming that the co-use of Cs and K as an alkali metal and the addition of the phosphate ($PO_4^-$) type precursor as a transition metal component result in a heteropoly acid catalyst having excellent electronic properties of the metal components and excellent catalytic activity as well as improved selectivity.

The heteropoly acid catalyst of the present invention is defined as formula 1.

The heteropoly acid catalyst includes P, Mo and V, and Cs and K together as an alkali metal, and one or more metal components selected from the group consisting of Cu, Ag, Co, Pb, Mn and Ti (indicated as X in formula 1), one or more metal components selected from the group consisting of As, Sb, Bi, Zn and Nb (indicated as Y), and one or more metal components selected from the group consisting of Cr, La, Ce, Fe, Ni and Mg (indicated as Q).

The alkali metal and the metal components indicated as X and Y in formula 1 are included in the catalyst as precursors in the form of carbonate.

It is preferred that the metal component indicated as Q is included as a precursor in the form of phosphate represented by $Q(PO_4)_f$. Particularly, $CrPO_4$, $LaPO_4$, $CePO_4$, $FePO_4$, $Ni_3(PO_4)_2$, $Mg_2P_2O_7$, and their hydrates can be included as a phosphate precursor.

It is preferred that the alkali metal component K is included as a precursor in the form of carbonate. The carbonate precursor can be included with Sb among metal components indicated as Y in formula 1 by mixing with $SbKC_4H_4O_7$ (potassium antimonyl tartarate).

The backbone structure of the heteropoly acid catalyst of formula 1 is phosphomolybdate represented by $H_3PMo_{12}O_{40}$. This backbone structure is keggin structure in which 12 octahedral molybdenums (Mo) share their edges around a phosphate. Herein, a part of or the whole molybdenums (Mo) can be substituted with the oxide of the metal component indicated as X. That is, the heteropoly acid has the structure of phosphomolybdate but its catalytic activity might be changed by electronic effect. The substituted oxidation number and the amount thereof can determine the number of cation to be bound. For example, when $Mo^{+6}$ is substituted with $V^{+5}$, the number of cation is increased from 3 to 4. And hydrogen ion can be substituted with alkali metal, alkali earth metal or transition metal, ammonium ion or pyridine ion. The substitution of cation results in the generation of secondary or tertiary structure. The physical properties of a catalyst such as surface area, pore volume and pore distribution can be regulated by the control of such secondary or tertiary structure to improve the capability of the catalyst.

The heteropoly acid catalyst is generally dried at 100-150° C. and then extruded by an extruder into a regular shape as a catalyst. Extrusion is very important because it directly affects the physical strength of a catalyst. To improve the strength of a catalyst, proper amount of distilled water and glass fiber can be added. The glass fiber contains Ca, Si, Al, etc, which are excluded from the category of effective catalyst elements of the present invention.

The extruded product is a cylindrical catalyst which is 5 mm in diameter and 5 mm in length. This cylindrical catalyst proceeds to firing at 350-500° C. in the presence of air or nitrogen. During the firing, volatile substances included in the precursor of a catalyst are eliminated. A part of pyridine is also eliminated during the firing and distilled water remaining as water of crystallization is slowly eliminated.

Y. Wang et al reported that $FePO_4$ was reduced at the temperature of at least 550° C. confirmed by TPR (Temperature Programmed Reduction) experiment which is designed to observe reduction by slowly providing hydrogen (Catal. Today 93 (2004) 155.). During the reduction, $Fe_2P_2O_7$ is generated but it changes into a stable $FePO_4$ in the presence of oxygen, even with a very small amount. Therefore, it is suggested that $FePO_4$ remains very stable at 400° C., the temperature for heat-treatment of the catalyst of the invention, and under oxidation condition of the invention. Other metals having $PO_4$ as anions are all confirmed to be stable at the temperature of at least 700° C.

The method of preparing a heteropoly acid catalyst of the present invention comprises the following steps; (a) preparing an aqueous solution by mixing $MoO_3$, $V_2O_5$ and $H_3PO_4$ with distilled water; (b) preparing a slurry by adding an aqueous solution prepared by mixing Cs and K precursors, a metal precursor and pyridine to the prepared aqueous solution; and (c) drying and firing the slurry.

In step (a), $MoO_3$, $V_2O_5$ and $H_3PO_4$ are mixed with distilled water and this mixture is heated at the temperature of at least 80° C., followed by reaction for at least 24 hours to prepare an aqueous solution. The prepared aqueous solution contains non-reacted solids which are separated to calculate the concentration of the produced heteropoly acid represented by $H_xPMoV_yO_z$ in the aqueous solution.

In step (b), Cs and K precursors, a metal precursor and pyridine are mixed with distilled water to prepare an aqueous solution. This aqueous solution is loaded in the aqueous solution prepared in step (a) with stirring at 20-60° C. to prepare a slurry, followed by reaction of the slurry at 70° C. The reaction is terminated by lowering the temperature to room temperature.

The metal precursor of step (b) is the precursor of metal component X which is one or more metal components selected from the group consisting of Cu, Ag, Co, Pb, Mn and Tl; metal component Y which is one or more metal components selected from the group consisting of As, Sb, Bi, Zn and Nb; or metal component Q which is one or more metal components selected from the group consisting of Cr, La, Ce, Fe, Ni and Mg.

The Cs and K precursors above can be a carbonate precursor.

The metal component K can be a carbonate precursor. Among carbonate precursors and metal components indicated as Y of formula 1, a Sb containing precursor such as $SbKC_4H_4O_7$ (potassium antimonyl tartarate) is preferred. At this time, when Sb and K are equal in equivalent, $SbKC_4H_4O_7$ (potassium antimonyl tartarate) can be used alone. When Sb and K are not equal in equivalent, $K_2CO_3$ is added to regulate the equivalent. When the equivalent of Sb is larger, the mixed solution of $Sb_2O_3$ and tartaric acid is added to regulate the equivalent.

The metal components indicated as X and Y can be a carbonate precursor and the metal component indicated as Q can be a phosphate precursor such as $Q(PO_4)_f$. Particularly, such phosphate precursors as $CrPO_4$, $LaPO_4$, $CePO_4$, $FePO_4$, $Ni_3(PO_4)_2$, $Mg_2P_2O_7$, and their hydrates can be used.

The aqueous solution containing Cs and K precursors and a metal precursor is preferably loaded at 20-60° C. Within this temperature range, loss resulted from unnecessary cooling is prevented and reaction speed can be easily regulated because carbonate is not decomposed and rather decomposed slowly when the temperature reaches 60° C., leading to the preparation of an excellent catalyst.

In step (c), the slurry prepared in step (b) is dried and fired to give a catalyst.

To remove distilled water used as a solvent, the slurry can be dried by filtration, vacuum drying or heat drying in an oven.

The dried slurry is pulverized, which is mixed with glass fiber, followed by extruding into a pellet in 5 mm×5 mm. The extruded product is fired at 300-500° C. in the presence of air to give a final catalyst.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

Example 1

To 1 l of distilled water were added 200 g of molybdenum oxide ($MoO_3$), 5.27 g of vanadium oxide ($V_2O_5$) and 14.69 g of $H_3PO_4$, followed by stirring at 80° C. for 36 hours. Upon completion of the reaction, the temperature was lowered to room temperature to terminate the reaction. As a result, 993.33 ml of the aqueous solution containing 30.9 g of non-reacted solid $MoO_3$ was obtained.

The prepared aqueous solution was loaded in a 2 l reactor equipped with a stirrer and the temperature therein was maintained at 50° C. To the reactor was added the aqueous solution prepared by mixing 23.92 g of $Cs_2CO_3$, 2.16 g of $Cu(OH)_2$—$CuCO_3$, 3.27 g of $SbKC_4H_4O_7$, 0.34 g of $K_2CO_3$, 0.34 g of $FePO_4.2H_2O$ and 34 g of pyridine with 300 ml of distilled water to prepare a slurry. The slurry was reacted at 70° C. for 3 hours and the temperature was lowered to room temperature to terminate the reaction.

The slurry was filtered and then the separated slurry was dried in a 120° C. oven for 12 hours. The dried slurry was pulverized, to which glass fiber was added by 5 wt %. The mixture proceeded to extrusion to give a 5 mm×5 mm pellet, followed by firing at 400° C. for 5 hours to give a catalyst.

The composition of the prepared catalyst is $PMo_{12}V_{0.5}Cs_{1.5}K_{0.15}Cu_{0.2}Sb_{0.1}(FePO_4)_{0.035}O_x$. The elements detected in glass fiber such as Ca, Si or Al are excluded from the composition of the catalyst.

Example 2

An experiment was performed by the same manner as described in example 1 except that 1.02 g of $K_2CO_3$ was used and a solution prepared by dissolving 1.69 g of $Sb_2O_3$ and 5 g of tartaric acid in 10 cc of distilled water was used instead of $SbKC_4H_4O_7$.

The composition of the prepared catalyst was $PMo_{12}V_{0.5}Cs_{1.5}K_{0.15}Cu_{0.2}Sb_{0.1}(FePO_4)_{0.035}O_x$.

Example 3

An experiment was performed by the same manner as described in example 1 except that 0.53 g of $LaPO_4.2H_2O$ was used instead of 0.34 g of $FePO_4.2H_2O$.

The composition of the prepared catalyst was $PMo_{12}V_{0.5}Cs_{1.5}K_{0.15}Cu_{0.2}Sb_{0.1}(LaPO_4)_{0.035}O_x$.

Comparative Example 1

An experiment was performed by the same manner as described in example 1 except that 0.37 g of $Fe(NO_3)_3.9H_2O$ was used instead of 0.34 g of $FePO_4.2H_2O$.

The composition of the prepared catalyst was $PMo_{12}V_{0.5}Cs_{1.5}K_{0.15}Cu_{0.2}Sb_{0.1}Fe_{0.035}O_x$.

Experimental Example

The heteropoly acid catalysts produced in examples 1-3 and comparative example 1 were used for gas phase oxidation of methacrolein by the following processes.

A ¾ inch steel reaction tube surrounded by three 15 cm long electrical furnaces whose temperature could be independently regulated was filled with each catalyst respectively. The raw material gas prepared by mixing 3.6 V % of methacrolein, 9.2 V % of oxygen, 76.9 V % of nitrogen and 10.3 V % of water vapor with the gas obtained in the reaction step 1 was serially injected into the reactor under the normal pressure. The temperature of the reactor was regulated as 290° C. by heat medium equipped in the outside of the steel reaction tube. Oxidation was induced at the space velocity of 960 h$^{-1}$(STP). The product was analyzed by real-time gas chromatography (GC).

Methacrolein conversion rate, methacrylic acid selectivity and yield were calculated by mathematical formulas 1-3 and the results are shown in Table 1.

Methacrolein conversion rate (%)=[mol of reacted methacrolein/mol of provided methacrolein]×100    MathFigure 1

Methacrylic acid selectivity (%)=[mol of formed methacrylic acid/mol of reacted methacrolein]×100    MathFigure 2

Yield (%)=[mol of formed methacrylic acid/mol of provided methacrolein]×100=conversion rate× selectivity    MathFigure 3

TABLE 1

|  | Methacrolein conversion rate (%) | Methacrylic acid selectivity (%) | Methacrylic acid yield (%) |
|---|---|---|---|
| Example 1 | 74.37 | 79.67 | 59.25 |
| Example 2 | 74.30 | 79.34 | 58.95 |
| Example 3 | 74.10 | 77.13 | 57.15 |
| Comparative Example 1 | 70.21 | 75.48 | 52.99 |

As shown in table 1, the heteropoly acid catalysts prepared in examples 1-3 contain Cs and K together as an alkali metal and a phosphate transition metal, so that the catalysts have excellent methacrolein conversion rate and methacrylic acid selectivity, compared with the catalyst of comparative example 1.

INDUSTRIAL APPLICABILITY

As explained hereinbefore, the present invention provides a novel heteropoly acid catalyst having excellent methacrolein conversion rate, methacrylic acid selectivity and yield.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A heteropoly acid catalyst represented by the following formula 1, $$PMo_{12}V_aCs_bK_cX_dY_e(Q(PO_4)_f)_gO_x$$ [Formula 1]

Wherein, X is one or more metal components selected from the group consisting of Cu, Ag, Co, Pb, Mn and Tl; Y is one or more metal components selected from the group consisting of As, Sb, Bi, Zn and Nb; Q is one or more metal components selected from the group consisting of Cr, La, Ce, Fe, Ni and Mg; a is $0.1<a<3$; b is $0.5<b<3$; c is $0<c<1$; d is $0<d<3$; e is $0<e<3$; f is $0.5<f<3$; g is $0.001<g<3$; x is the number satisfied with atomic values of a, b, c, d, e, f and g.

2. The heteropoly acid catalyst according to claim 1, wherein $Q(PO_4)$ is one or more compounds selected from the group consisting of $CrPO_4$, $LaPO_4$, $CePO_4$, $FePO_4$, $Ni_3(PO_4)_2$, $Mg_2P_2O_7$ and their hydrates.

3. A method of preparing the heteropoly acid catalyst of claim 1, which is comprised of the following steps:
   (a) preparing an aqueous solution by mixing $MoO_3$, $V_2O_5$ and $H_3PO_4$ with a distilled water;
   (b) preparing a slurry by adding dropwise an aqueous solution prepared by mixing Cs and K precursors, a metal precursor and pyridine to the prepared aqueous solution; and
   (c) drying and firing the slurry.

4. The method of preparing the heteropoly acid catalyst according to claim 3, wherein the metal precursor of step (b) is the precursor of metal component X which is one or more metal components selected from the group consisting of Cu, Ag, Co, Pb, Mn and Tl; metal component Y which is one or more metal components selected from the group consisting of As, Sb, Bi, Zn and Nb; or metal component Q which is one or more metal components selected from the group consisting of Cr, La, Ce, Fe, Ni and Mg.

5. The method of preparing the heteropoly acid catalyst according to claim 4, wherein the precursor of metal element Q is the phosphate precursor represented by $Q(PO_4)_f$ and one or more compounds selected from the group consisting of $CrPO_4$, $LaPO_4$, $CePO_4$, $FePO_4$, $Ni_3(PO_4)_2$, $Mg_2P_2O_7$ and their hydrates.

6. The method of preparing the heteropoly acid catalyst according to claim 3, wherein the K precursor of step (b) is a carbonate precursor or a mixture of a carbonate precursor and $SbKC_4H_4O_7$.

* * * * *